(12) United States Patent
Morris et al.

(10) Patent No.: US 8,784,800 B2
(45) Date of Patent: Jul. 22, 2014

(54) METHOD OF DELIVERING CELL THERAPY TO A TARGET SITE

(75) Inventors: Mary M. Morris, Shoreview, MN (US);
Kenneth Gardeski, Plymouth, MN (US); Laurent Verard, Andover, MA (US); Kevin Thomas Wu, Bellevue, WA (US); Michael R. Neidert, Salthill (IE)

(73) Assignee: Medtronic, Inc., Minneapolis, MN (US)

( * ) Notice: Subject to any disclaimer, the term of this patent is extended or adjusted under 35 U.S.C. 154(b) by 1008 days.

(21) Appl. No.: 12/400,059

(22) Filed: Mar. 9, 2009

(65) Prior Publication Data

US 2010/0226903 A1  Sep. 9, 2010

(51) Int. Cl.
*A61K 35/12* (2006.01)
*A61K 35/00* (2006.01)
*A61K 49/04* (2006.01)
*A61K 49/06* (2006.01)
*A61K 35/28* (2006.01)
*A61K 35/32* (2006.01)

(52) U.S. Cl.
USPC ............ 424/93.7; 424/9.3; 424/9.4; 424/548; 424/577; 600/434; 600/507

(58) Field of Classification Search
CPC .......... A61B 6/12; A61B 6/481; A61B 6/504; A61B 6/541; A61B 19/5244
See application file for complete search history.

(56) References Cited

U.S. PATENT DOCUMENTS 5,983,126 A  11/1999  Wittkampf et al.
6,151,525 A  11/2000  Soykan et al.
6,272,370 B1 *  8/2001  Gillies et al. ................. 600/411
6,416,510 B1  7/2002  Altman et al.
6,547,787 B1  4/2003  Altman et al.
6,636,757 B1  10/2003  Jascob et al.

(Continued)

FOREIGN PATENT DOCUMENTS

WO  WO-2005073915  8/2005
WO  WO-2005120587  12/2005
WO  WO-2006060107  6/2006
WO  WO-2008073577  6/2008

OTHER PUBLICATIONS

Rickers, C., et al., "Applications of magnetic resonance imaging for cardiac stem cell therapy", Journal of Interventional Cardiology, vol. 17, No. 1, pp. 37-46.*

(Continued)

*Primary Examiner* — Nashaat Nashed
*Assistant Examiner* — William W Moore
(74) *Attorney, Agent, or Firm* — Carol F. Barry

(57) ABSTRACT

A method of delivering therapy to a target site. The method includes (a) obtaining a base image of the target site, (b) injecting a dose of a mix of a therapeutic agent and a contrast agent into a first injection location at the target site via a needle passing through a catheter, (c) collecting sequential fluoroscopic images of a contrast agent dispersion cloud at the first injection location, (d) determining a contrast agent dispersion area from the sequential fluoroscopic images, (e) determining a therapeutic agent dispersion area from the contrast agent dispersion area, (f) marking the therapeutic agent dispersion area on the base image of the target site, and (g) repeating (b) through (f) until the target site is substantially covered with overlapping therapeutic agent dispersion areas corresponding to a plurality of injections at a plurality of injection locations at the target site.

19 Claims, 15 Drawing Sheets

(56) References Cited

U.S. PATENT DOCUMENTS

| | | | |
|---|---|---|---|
| 6,716,190 | B1 | 4/2004 | Glines et al. |
| 7,130,700 | B2 | 10/2006 | Gardeski et al. |
| 7,155,288 | B2 | 12/2006 | Soykan et al. |
| 2004/0067221 | A1 | 4/2004 | Morris et al. |
| 2004/0097805 | A1 | 5/2004 | Verard et al. |
| 2004/0097806 | A1 | 5/2004 | Hunter et al. |
| 2004/0097965 | A1 | 5/2004 | Gardeski et al. |
| 2004/0138643 | A1 | 7/2004 | Seward et al. |
| 2004/0147963 | A1 | 7/2004 | Sommer et al. |
| 2005/0277889 | A1 | 12/2005 | Neidert et al. |
| 2005/0287125 | A1 | 12/2005 | Morris et al. |
| 2007/0053839 | A1* | 3/2007 | Zhang .................. 424/9.1 |
| 2007/0164900 | A1 | 7/2007 | Schneider et al. |
| 2008/0103537 | A1 | 5/2008 | Sigg et al. |

OTHER PUBLICATIONS

Beeri et al. New Efficient Catheter-Based System for Myocardial Gene Delivery. *Circulation*. 2002;106:1756-1759. Downloaded from circ.ahajournals.org by on Jan. 6, 2009.

Bogun et al. Electrogram Characteristics in Postinfarction Ventricular Tachycardia: Effect of Infarct Age. *J. Am. Coll. Cardiol.* published online Jul 27, 2005; doi:10.1016/j.jacc.2005.01.064. Downloaded from content.onlinejacc.org by on Dec. 29, 2008.

Dick et al. Magnetic Resonance Fluoroscopy Allows Targeted Delivery of Mesenchymal Stem Cells to Infarct Borders in Swine. *Circulation* 2003; 108:2899-2904. Downloaded from circ.ahajournals.org by on Jan. 6, 2009.

Frangioni and Najjar. In Vivo Tracking of Stem Cells for Clinical Trials in Cardiovascular Disease. *Circulation* 2004;110:3378-3384.

Krombach et al. MR-guided Percutaneous Intramyocardial Injection with an MR-compatible Catheter: Feasibility and Changes in T1 Values after Injection of Extracellular Contrast Medium in Pigs. *Radiology* May 2005; 235:487-494.

Opie and Dib. Surgical and Catheter Delivery of Autologous Myoblasts in Patients with Congestive Heart Failure. *Nature Clinical Practice; Cardiovascular Medicine*. Mar. 2006;3(1):S42-S45.

Ozturk et al. Magnetic Resonance Imaging-guided Vascular Interventions. *Top Magn Reson Imaging*. Oct. 2005; 16(5):369-381.

Perin and Silva. Stem Cell Therapy in End-Stage Ischaemic Heart Failure: A Catheter-Based Therapeutic Strategy Targeting Myocardial Viability. *European Heart Journal Supplements* 2006;8;H:H46-H51 doi:10.1093/eurheart/sul066.

Saborowski and Saeed. An Overview on the Advances in Cardiovascular Interventional MR Imaging. *Magn Reson Matter Phy* 2007; 20:117-127.

Sherman et al. Catheter-Based Delivery of Cells to the Heart. *Nature Clinical Practice; Cardiovascular Medicine*. Mar. 2006;3(1):S57-S84.

Sherman, Warren. Cell Therapy in the Cath Lab for Heart Failure: A Look at MyoCell® Therapy and the SEISMIC Trial [Interview]. *Cath Lab Digest*. May 2008;16;5:1-4.

Silva et al. Catheter-Based Trans-endocardial Delivery of Autologous Bone-Marrow-Derived Mononuclear Cells in Patients Listed for Heart Transplantation. Clinical Investigation. *Tex Heart Inst J* 2004;31(3):214-219.

Smits et al. Catheter-Based Intramyocardial Injection of Autologous Skeletal Myoblasts as a Primary Treatment of Ischemic Heart Failure: Clinical Experience with Six-Month Follow-Up. *J. Am. Coll. Cardiol.* 2003;42:2063-2069 doi:10.1016/j.jacc.203.06.017. Downloaded from content.onlinejacc.org by on Dec. 29, 2008.

Smits et al. Myocardial Repair by Percutaneous Cell Transplantation of Autologous Skeletal Myoblast as a Stand Alone Procedure in Post Myocardial Infarction Chronic Heart Failure Patients. *EuroInterv.* 2006;1:417-424.

\* cited by examiner

TABLE 1

| Tissue Type | Peak Size | Duration Size | Peak Intensity (I) | dI/dt |
|---|---|---|---|---|
| Muscle | Moderate | Long | High | Moderate |
| Scar | Moderate | Long | High | Low |
| Blood Lumen Heart | Low | Short | Low | High then NA |
| Blood Vessel | Low to mod. | Short | High | High then NA |
| Pericardial Space | Mod. to high | Long | Moderate | High then low |

FIG. 10

TABLE 2

| Tissue Type | β |
|---|---|
| Muscle | 0.4 to 0.8 |
| Scar | 0.2 to 0.8 |
| Pericardial space | 0 |
| Blood lumen of heart | 0 |
| Blood vessel | 0 to 0.2 |

FIG. 11

METHOD OF DELIVERING CELL THERAPY TO A TARGET SITE

INTRODUCTION

Recent animal studies, pre-clinical and clinical investigations consider the therapeutic effect of catheter-based delivery of cells to the heart for treating conditions such as congestive heart failure, ischemic heart failure, post myocardial infarction in chronic heart failure and other cardiac conditions.

The present teachings provide a method of delivering cell therapy to a target site and populating the target site with injectable therapeutic agents.

SUMMARY

The present teachings provide methods of delivering therapy to a target site. In one aspect the includes (a) obtaining a base image of the target site, (b) injecting a dose of a mix of a therapeutic agent and a contrast agent into a first injection location at the target site via a needle passing through a catheter, (c) collecting sequential fluoroscopic images of a contrast agent dispersion cloud at the first injection location, (d) determining a contrast agent dispersion area from the sequential fluoroscopic images, (e) determining a therapeutic agent dispersion area from the contrast agent dispersion area, (f) marking the therapeutic agent dispersion area on the base image of the target site, and (g) repeating (b) through (f) until the target site is substantially covered with overlapping therapeutic agent dispersion areas corresponding to a plurality of injections at a plurality of injection locations at the target site.

In another aspect, the method includes obtaining a base image of the target site, navigating a catheter including a delivery needle to the target site, injecting through the needle a first dose of a mix of a therapeutic agent and a contrast agent into a first injection location at the target site, and collecting sequential fluoroscopic images of a contrast agent dispersion cloud at the first injection location. The method further includes determining a contrast agent dispersion region from the sequential fluoroscopic images of the first injection location, identifying a tissue type of the first injection location, determining a therapeutic agent dispersion region from the contrast agent dispersion region of the first injection location, marking the therapeutic agent dispersion region of the first injection location on the base image of the target site, and injecting through the needle a second dose of a mix of a therapeutic agent and a contrast agent into a second injection location different from the first injection location at the target site.

In a further aspect, the method includes (a) obtaining a base image of the target site, (b) injecting a dose of a mix of a therapeutic agent and an imaging agent into a first injection location at the target site, collecting sequential images of an imaging agent visible region at the first injection location, determining an imaging agent dispersion area from the sequential images, determining a therapeutic agent dispersion area from the imaging agent dispersion area, optionally marking the therapeutic agent dispersion area on the base image of the target site, and (g) repeating (b) through (f) until the target site is substantially covered with overlapping therapeutic agent dispersion areas corresponding to a plurality of injections at a plurality of injection locations at the target site.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 10 is a table providing characteristics of the contrast dispersion cloud for various tissue types according to the present teachings;

FIG. 11 is a table providing a range of values for parameter β for determining a cell dispersion area from a contrast cloud dispersion area according to the present teachings;

DESCRIPTION OF VARIOUS ASPECTS

The following description is merely exemplary in nature and is in no way intended to limit the present teachings, applications, or uses. The devices disclosed herein include exemplary leads, catheters, navigation and imaging systems, which, however, can be varied according to particular procedures or embodiments.

The present teachings are generally directed to a method of delivering therapy via cell agents or other biologic, drug, or therapeutic agents and materials to a target site, such as a cardiac tissue, including tissue that may be defective, damaged or in danger of suffering damage. More particularly, the present teachings provide a method for interactively determining a therapy dispersion area in the tissue by monitoring a therapy/contrast agent dispersion cloud in the tissue, such that the target area can be covered by the therapy dispersion cloud.

The present teachings can be used in conjunction with various exemplary navigation systems, such as those described in commonly assigned U.S. Pat. No. 6,636,757, and in currently pending and commonly assigned patent application Ser. No. 10/299,969, filed Nov. 19, 2003 (2004/0097806) and Ser. No. 10/619,126, filed Jul. 14, 2003 (2004/0097805), the disclosures of each of which are incorporated herein by reference. An exemplary navigation system is described below in connection with FIG. 1. The present teachings can also be used with various exemplary therapy delivery systems, such as those disclosed in currently pending and commonly assigned patent application Ser. No. 10/867,059, filed Jun. 14, 2004 (2005/0277889), and Ser. No. 11/322,393, filed Dec. 30, 2005 (2007/0164900), the disclosures of each of which are incorporated herein by reference. An exemplary modular therapy delivery system is described below in connection with FIGS. 2 and 3 and can be used with the navigation system and navigation catheter of FIG. 10, or with a steerable catheter as shown in FIG. 3A. Alternatively, an integrated steerable navigation/therapy delivery catheter can be used, such as the integrated catheter disclosed in U.S. Pat. No. 7,130,700 issued Oct. 31, 2006 and incorporated herein by reference. An exemplary embodiment of the integrated catheter 440 is illustrated in FIGS. 3B and 3C and described below.

Figure 1:
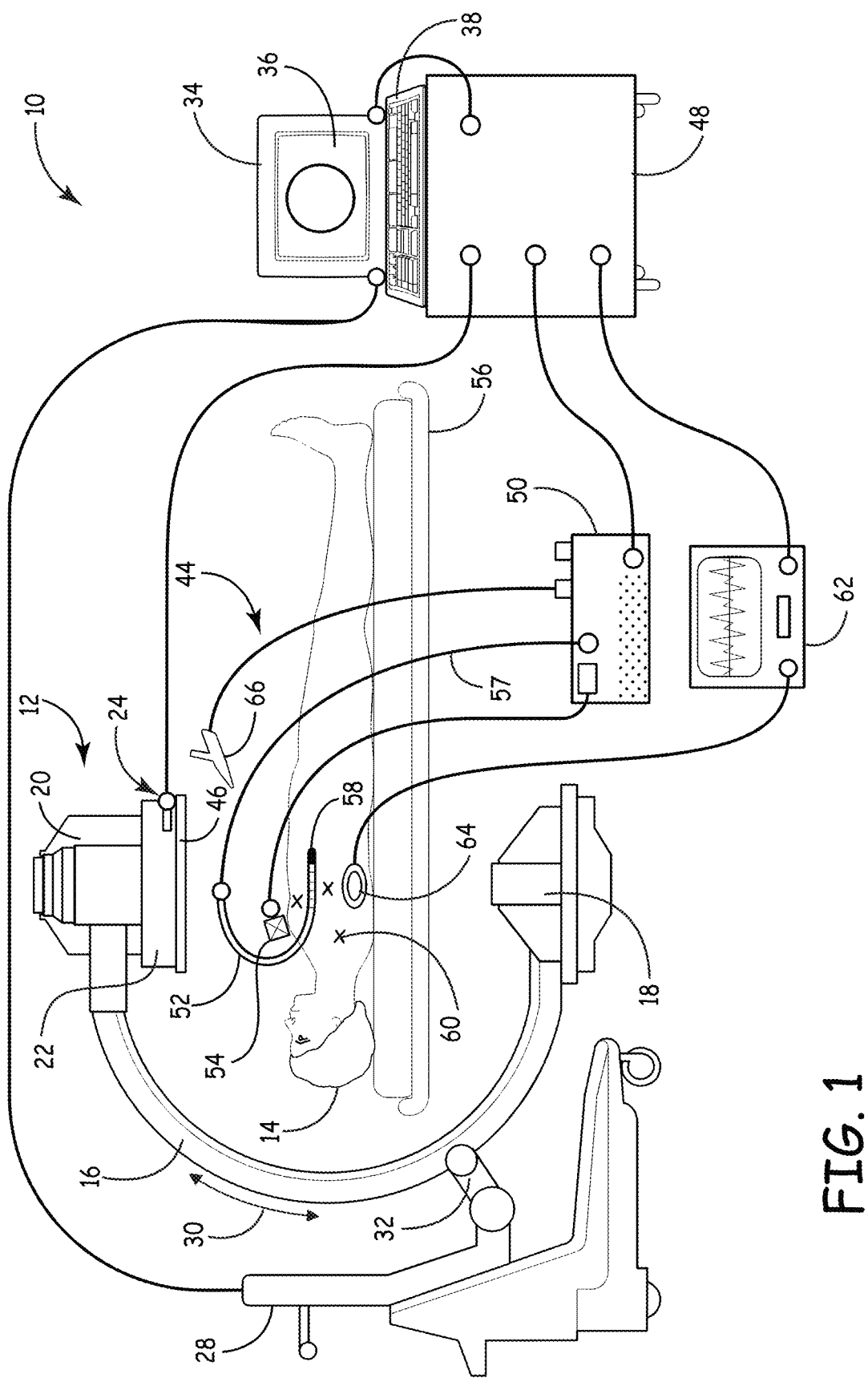
FIG. 1 is a diagram of an exemplary catheter navigation system.

FIG. 1 is a diagram illustrating an overview of an exemplary image-guided catheter navigation system 10 for use in non-line-of-site navigating of a catheter during cardiac therapy or any other soft tissue therapy, including the cell/drug delivery therapy discussed herein. It should further be noted that the navigation system 10 may be used to navigate any other type of instrument or delivery system, including guide wires, needles, drug delivery systems, cell delivery systems, gene delivery systems and biopsy systems. Moreover, these instruments may be used for cardiac therapy or any other therapy in the body or be used to navigate or map any other regions of the body, such as moving body structures. However, each region of the body poses unique requirements to navigate, as disclosed herein. For example, the navigation system 10 can address multiple cardiac, neurological, organ and other soft tissue therapies, including drug delivery, cell transplantation, gene delivery, electrophysiology ablations, transmyocardial vascularization (TMR), biopsy guidance, and virtual echography imaging.

Figure 1A:
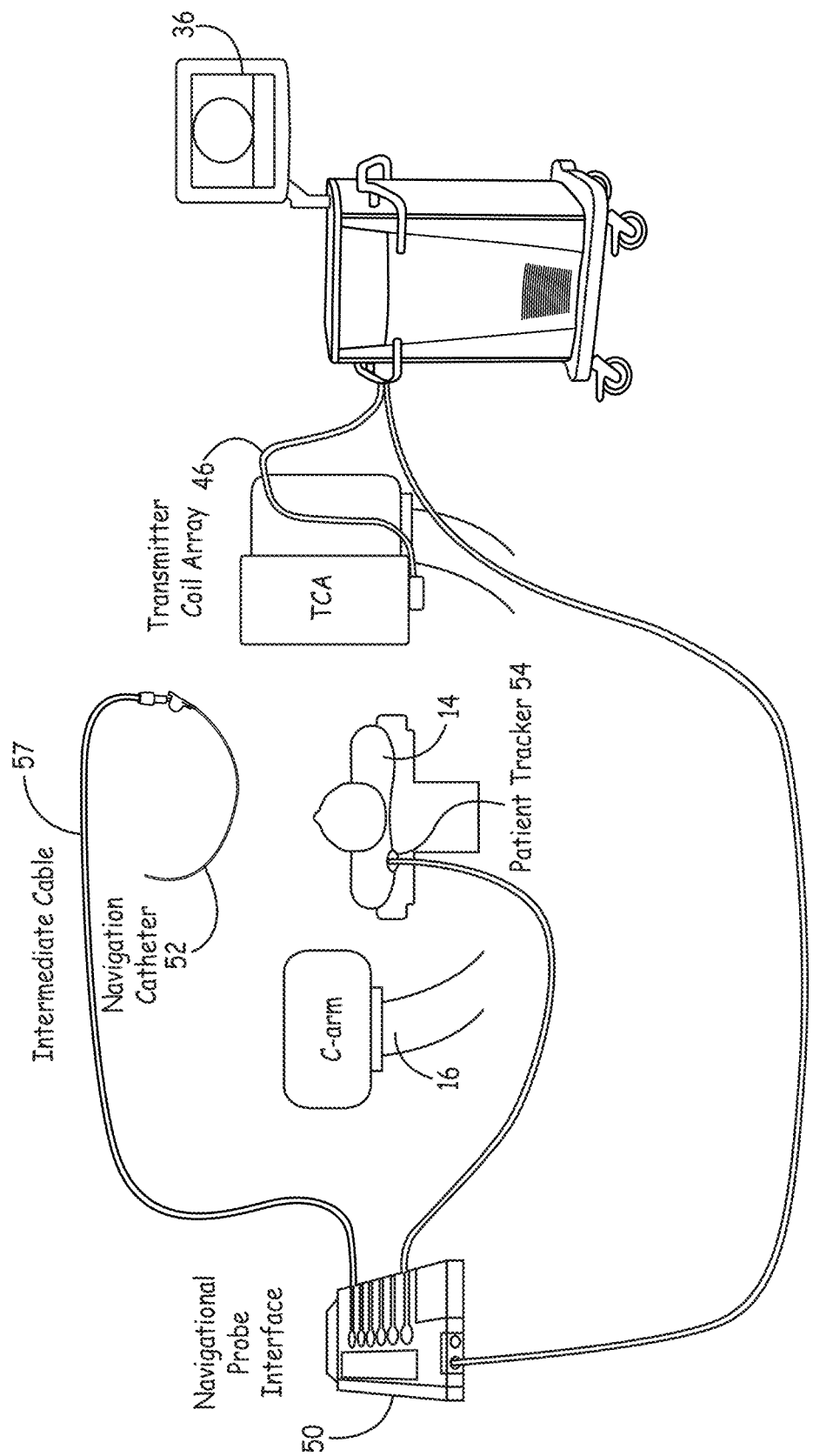
FIG. 1A is a diagram of an exemplary catheter navigation system.
Figure 1B:
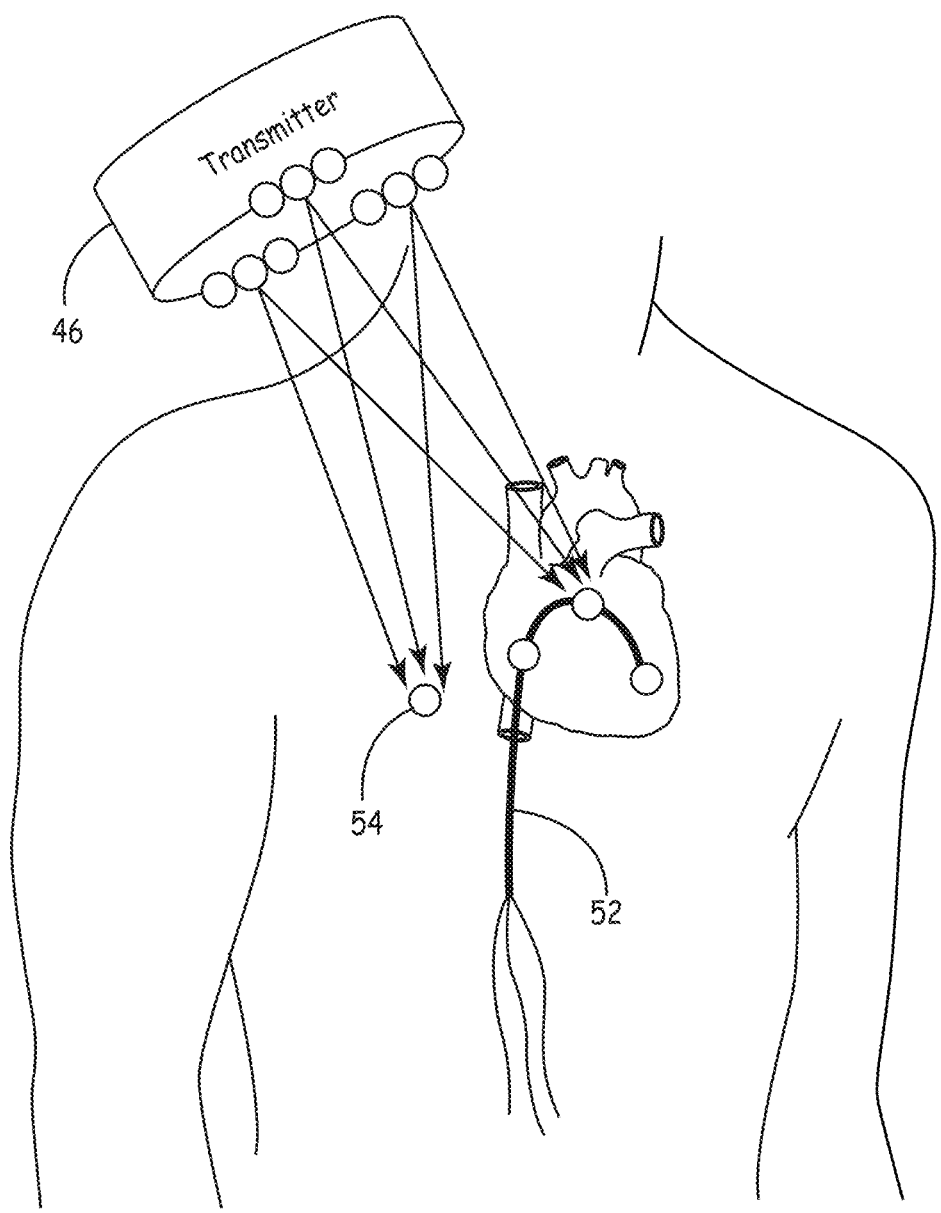
FIG. 1B is an environmental view of a catheter of the navigation system of FIG. 1A.

Referring to FIGS. 1, 1A and 1B, the navigation system 10 may include an imaging device 12 that is used to acquire pre-operative or real-time images of a patient 14. The imaging device 12 can be a fluoroscopic x-ray imaging device that may include a C-arm 16 having an x-ray source 18, an x-ray receiving section 20, an optional calibration and tracking target 22 and optional radiation sensors 24. The calibration and tracking target 22 can include calibration markers. A C-arm controller 28 can be used to capture the x-ray images received at the receiving section 20 and store the images for later use. The C-arm controller 28 may also control the rotation of the C-arm 16. For example, the C-arm 16 may move in the direction of arrow 30 or rotate about the long axis of the patient 14, allowing anterior or lateral views of the patient 14 to be imaged. Each of these movements involves rotation about a mechanical axis 32 of the C-arm 16. In this example, the long axis of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

In operation, the imaging device 12 generates x-rays from the x-ray source 18 that propagate through the patient 14 and calibration and/or tracking target 22, into the x-ray receiving section 20. The receiving section 20 generates an image representing the intensities of the received x-rays. Typically, the receiving section 20 includes an image intensifier that first converts the x-rays to visible light and a charge coupled device (CCD) video camera that converts the visible light into digital images. Receiving section 20 may also be a digital device that converts x-rays directly to digital images, thus potentially avoiding distortion introduced by first converting to visible light. With this type of digital C-arm, which is generally a flat panel device, the optional calibration and/or tracking target 22 and an associated calibration process may be eliminated. Also, the calibration process may be eliminated or not used at all for cardiac therapies. Alternatively, the imaging device 12 may only take a single image with the calibration and tracking target 22 in place. Thereafter, the calibration and tracking target 22 may be removed from the line-of-sight of the imaging device 12.

Two dimensional fluoroscopic images taken by the imaging device 12 can be captured and stored in the C-arm controller 28. Multiple two-dimensional images taken by the imaging device 12 may also be captured and assembled to provide a larger view or image of a whole region of a patient, as opposed to being directed to only a portion of a region of the patient. These images are then forwarded from the C-arm controller 28 to a controller or work station 34 having a display 36 and a user interface 38. The work station 34 provides facilities for displaying on the display 36, saving, digitally manipulating, or printing a hard copy of the received images. The user interface 38, which may be a keyboard, mouse, touch pen, touch screen or other suitable device, allows a physician or user to provide inputs to control the imaging device 12, via the C-arm controller 28, or adjust the display settings of the display 36. The work station 34 may also direct the C-arm controller 28 to adjust the rotational axis 32 of the C-arm 16 to obtain various two-dimensional images along different planes in order to generate representative two-dimensional and three-dimensional images. When the x-ray source 18 generates the x-rays that propagate to the x-ray receiving section 20, the radiation sensors 24 sense the presence of radiation, which is forwarded to the C-arm controller 28, to identify whether or not the imaging device 12 is actively imaging. This information is also transmitted to a coil array controller 48, further discussed herein. Alternatively, a person or physician may manually indicate when the imaging device 12 is actively imaging or this function can be built into the x-ray source 18, x-ray receiving section 20, or the control computer 28.

With continued reference to FIGS. 1, 1A, and 1B, navigation system 10 can further include an electromagnetic navigation or tracking system 44 that includes a transmitter coil array 46, the coil array controller 48, a navigation probe interface 50, a navigation or electromagnetic catheter or insert 52 or any other type of instrument and a dynamic reference frame 54. Further, it should further be noted that the entire tracking system 44 or parts of the tracking system 44 may be incorporated into the imaging device 12, including the work station 34 and radiation sensors 24. Incorporating the tracking system 44 will provide an integrated imaging and tracking system. Any combination of these components may also be incorporated into the imaging device 12, which again can include a fluoroscopic C-arm imaging device or any other appropriate imaging device.

In the exemplary illustration of FIG. 1, the transmitter coil array 46 is shown attached to the receiving section 20 of the C-arm 16. However, it should be noted that the transmitter coil array 46 may also be positioned at any other location as well. For example, the transmitter coil array 46 may be positioned at the x-ray source 18, within or atop the operating room table 56 positioned below the patient 14, on side rails associated with the table 56, or positioned on the patient 14 in proximity to the region being navigated, such as on the patient's chest. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999, and U.S. Pat. No. 5,592,939, entitled "Method and System for Navigating a Catheter Probe," issued Jan. 14, 1997, each of which are incorporated herein by reference.

The transmitter coil array 46 can be controlled or driven by the coil array controller 48. The coil array controller 48 can drive each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induce currents in sensors 58 positioned in the electromagnetic catheter 52. These induced signals from the electromagnetic catheter 52 are delivered to the navigation probe interface 50 via a connection cable 57 and subsequently forwarded to the coil array controller 48. The navigation probe interface 50 provides all the necessary electrical isolation for the navigation system 10. The navigation probe interface 50 also includes amplifiers, filters and buffers required to directly interface with the sensors 58 in electromagnetic catheter 52. Alternatively, the electromagnetic catheter 52 may employ a wireless communications channel as opposed to being coupled directly to the navigation probe interface 50.

The electromagnetic catheter 52 may be equipped with at least one, and generally multiple, localization sensors 58. The electromagnetic catheter 52 may also be a steerable catheter that includes a handle at a proximal end and the multiple location sensors 58 fixed to the catheter body and spaced axially from one another along the distal segment of the electromagnetic catheter 52. The electromagnetic catheter 52, as shown in FIG. 1, includes four localization sensors 58. The localization sensors 58 are generally formed as electromagnetic receiver coils, such that the electromagnetic field generated by the transmitter coil array 46 induces current in the electromagnetic receiver coils or sensors 58. The electromagnetic catheter 52 may also be equipped with one or more sensors, which are operable to sense various physiological signals. For example, the electromagnetic catheter 52 may be provided with electrodes for sensing myopotentials or action potentials. An absolute pressure sensor may also be included, as well as other electrode sensors. The electromagnetic catheter 52 may also be provided with an open lumen to allow the delivery of a medical device or pharmaceutical/cell/gene agents. For example, the electromagnetic catheter 52 may be used as a guide catheter for deploying a medical lead, such as a cardiac lead for use in cardiac pacing and/or defibrillation or tissue ablation. The open lumen may alternatively be used to locally deliver pharmaceutical agents, cell, or genetic therapies. A representative catheter which may be used is that which is disclosed in U.S. patent application Ser. No. 10/619, 216, filed Jul. 14, 2003, (2004/0097805), which is hereby incorporated by reference.

In an alternate aspect, the electromagnetic sources or generators may be located within the electromagnetic catheter 52 and one or more receiver coils may be provided externally to the patient 14, forming a receiver coil array similar to the transmitter coil array 46. In this regard, the sensor coils 58 would generate electromagnetic fields, which would be received by the receiving coils in the receiving coil array similar to the transmitter coil array 46. Other types of localization sensors or systems may also be used, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. Other types of tracking systems include optical, acoustic, electrical field, RF and accelerometers. Accelerometers enable both dynamic sensing due to motion and static sensing due to gravity. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the electromagnetic tracking system 44 can also coupled to the navigation probe interface 50 to forward the information to the coil array controller 48. The dynamic reference frame 54 can be a small magnetic field detector that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation, further discussed herein. The dynamic reference frame 54 can be configured as a pair of orthogonally oriented coils, each having the same center or may be configured in any other non-coaxial coil configuration. The dynamic reference frame 54 may be affixed externally to the patient 14, adjacent to the region of navigation, such as on the patient's chest, as shown in FIG. 1 or on the patient's back. The dynamic reference frame 54 can be affixed to the patient's skin, by way of a stick-on adhesive patch. The dynamic reference frame 54 may also be removably attachable to fiducial markers 60 also positioned on the patient's body.

Alternatively, the dynamic reference frame 54 may be internally attached, for example, to the wall of the patient's heart or other soft tissue using a temporary lead that is attached directly to the heart. This provides increased accuracy since this lead will track the regional motion of the heart. Gating, as further discussed herein, will also increase the navigational accuracy of the system 10. An exemplary dynamic reference frame 54 and fiducial marker 60, is set forth in U.S. Pat. No. 6,381,485, entitled "Registration of Human Anatomy Integrated for Electromagnetic Localization," issued Apr. 30, 2002, which is hereby incorporated by reference. It should further be noted that multiple dynamic reference frames 54 may also be employed. For example, an external dynamic reference frame 54 may be attached to the chest of the patient 14, as well as to the back of the patient 14. Since certain regions of the body may move more than others due to motions of the heart or the respiratory system, each dynamic reference frame 54 may be appropriately weighted to increase accuracy even further. In this regard, the dynamic reference frame 54 attached to the back may be weighted higher than the dynamic reference frame 54 attached to the chest, since the dynamic reference frame 54 attached to the back is relatively static in motion.

The catheter and navigation system 10 can further include a gating device or an ECG or electrocardiogram device 62, which is attached to the patient 14, via skin electrodes 64, and in communication with the coil array controller 48. Respiration and cardiac motion can cause movement of cardiac structures relative to the electromagnetic catheter 52, even when the electromagnetic catheter 52 has not been moved. Therefore, localization data may be acquired on a time-gated basis triggered by a physiological signal. For example, the ECG or EGM signal may be acquired from the skin electrodes 64 or from a sensing electrode included on the electromagnetic catheter 52 or from a separate reference probe. A characteristic of this signal may be used as to gate or trigger image acquisition during the imaging phase with the imaging device 12. By event gating at a point in a cycle the image data and/or the navigation data, the icon of the location of the electromagnetic catheter 52 relative to the heart at the same point in the cardiac cycle may be displayed on the display 36, as discussed in co-pending and commonly assigned patent application Ser. No. 12/183,688, filed Jul. 31, 2008, the disclosure of which is incorporated herein by reference.

Additionally or alternatively, a sensor regarding respiration may be used to trigger data collection at the same point in the respiration cycle. Additional external sensors can also be coupled to the navigation system 10. These could include a capnographic sensor that monitors exhaled $CO_2$ concentration. From this, the end expiration point can be easily determined. The respiration, both ventriculated and spontaneous causes an undesirable elevation or reduction, respectively, in the baseline pressure signal. By measuring systolic and diastolic pressures at the end expiration point, the coupling of respiration noise is minimized. As an alternative to the $CO_2$ sensor, an airway pressure sensor can be used to determine end expiration.

Briefly, the navigation system 10 operates as follows. The navigation system 10 creates a translation map between all points in the radiological image generated from the imaging device 12 and the corresponding points in the patient's anatomy in patient space. After this map is established, whenever a tracked instrument, such as the electromagnetic catheter 52 or pointing device is used, the work station 34, in combination with the coil array controller 48 and the C-arm controller 28, uses the translation map to identify the corresponding point on the pre-acquired image, which is exhibited on display 36. This identification is known as navigation or localization. An icon representing the localized point or an instrument is shown on the display 36 within several two-dimensional image planes, as well as on three and four dimensional images and models.

To enable navigation, the navigation system 10 must be able to detect both the position of the patient's anatomy and the position of the electromagnetic catheter 52 or other surgical instrument. Knowing the location of these two items allows the navigation system 10 to compute and display the position of the electromagnetic catheter 52 in relation to the patient 14 on the radiological images. The tracking system 44 is employed to track the electromagnetic catheter 52 and the anatomy simultaneously.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the electromagnetic catheter 52 by measuring the field strength at the sensor 58 location. The dynamic reference frame 54 is fixed to the patient 14 to identify the location of the patient in the navigation field. The electromagnetic tracking system 44 continuously recomputes the relative position of the dynamic reference frame 54 and the electromagnetic catheter 52 during localization and relates this spatial information to patient registration data to enable image guidance of the electromagnetic catheter 52 within the patient 14.

Patient registration is the process of determining how to correlate the position of the instrument or electromagnetic catheter 52 on the patient 14 to the position on the diagnostic or pre-acquired images. To register the patient 14, the physician or user may use point registration by selecting and storing particular points from the pre-acquired images and then touching the corresponding points on the patient's anatomy with a pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial arrays or landmarks or fiducial markers 60. Again, the landmarks or fiducial markers 60 are identifiable on the images and identifiable and accessible on the patient 14. The fiducial markers 60 can be artificial landmarks that are positioned on the patient 14 or anatomical landmarks that can be easily identified in the image data. The system 10 may also perform registration using anatomic surface information or path information, further discussed herein. The system 10 may also perform 2D to 3D registration by utilizing the acquired 2D images to register 3D volume images by use of contour algorithms, point algorithms or density comparison algorithms, as is known in the art. An exemplary 2D to 3D registration procedure, as set forth in currently pending and co-owned U.S. patent application Ser. No. 10/644,680 filed Aug. 20, 2003 (2004/0215071), entitled "Method and Apparatus for Performing 2D to 3D Registration," which is incorporated herein by reference. The registration process may also be synched to an anatomical function, for example, by the use of the ECG device 62.

In order to maintain registration accuracy, the navigation system 10 continuously tracks the position of the patient 14 during registration and navigation. This is because the patient 14, dynamic reference frame 54, and transmitter coil array 46 may all move during the procedure, even when this movement is not desired. Therefore, if the navigation system 10 did not track the position of the patient 14 or area of the anatomy, any patient movement after image acquisition would result in inaccurate navigation within that image. The dynamic reference frame 54 allows the electromagnetic tracking system 44 to register and track the anatomy. Because the dynamic reference frame 54 is attached to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

Figure 2:
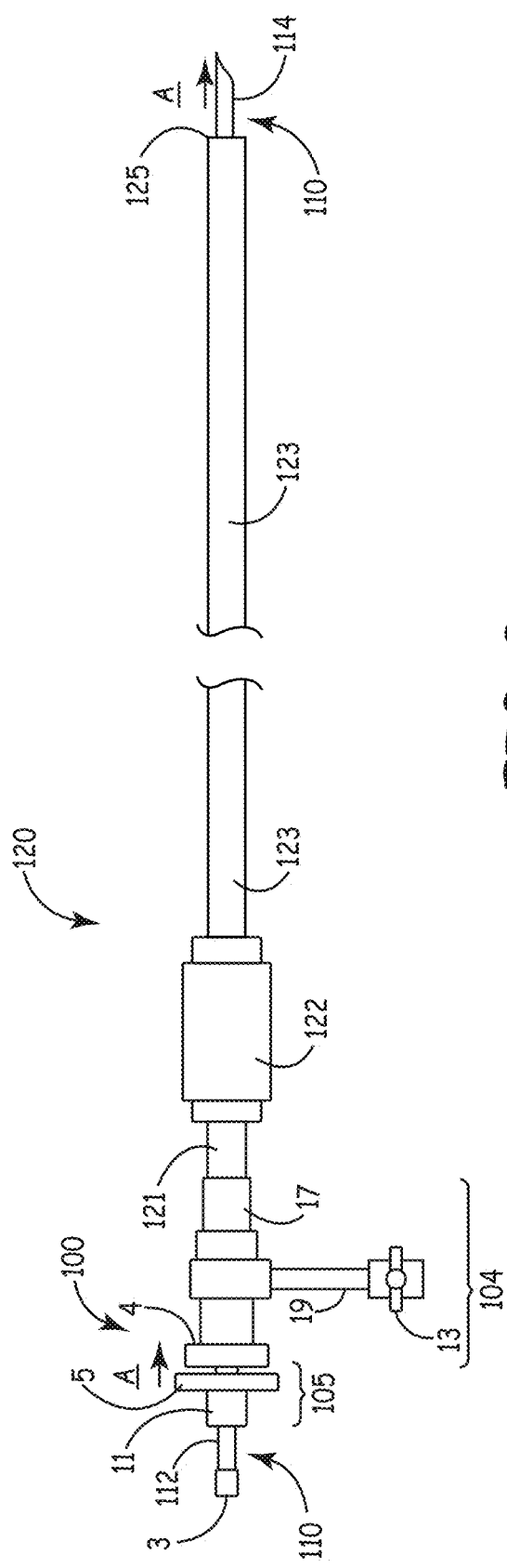
FIG. 2 is a side view of an exemplary modular injection system.

FIG. 2 is a plan view of an exemplary modular medical injection system according to one aspect of the present teachings. As illustrated in FIG. 2, the system can include an exemplary therapy delivery catheter 120 which can be used with the navigation system 10 of FIGS. 1, 1A, 1B, and include a navigation or electromagnetic catheter insert 52 that incorporates some or all features described in connection with FIG. 1. An actuator 100 can be joined to the delivery catheter 120 by means of a coupling or a connector 17 at a distal end of an actuator fitting 104, a lumen (not shown), which extends through a shaft 123, through a handle 122 of catheter 120 and through actuator 100. The actuator 100 can slidably engage an injection apparatus 110 whose needle tip 114 is shown extending out from a catheter distal end 125. FIG. 2 further illustrates injection apparatus 110 including an elongate shaft 112 and a fitting 3 terminating a proximal end of shaft 112. The fitting 3 can be adapted to couple injection apparatus 110 to a source, for example a syringe, for injection of therapeutic agents from the source through a lumen 113 (FIG. 3) of the injection apparatus 110. In the exemplary aspect of FIG. 2, the actuator 100 can further include a plunger 105 slidably engaged with fitting 104. The plunger 105 can include a valve 11 for reversibly gripping the shaft 112 of the injection apparatus 110 so that when an operator forces plunger 105 toward fitting 104 in the direction of arrow A, the shaft 112, being gripped by valve 11, is forced distally through catheter 120 so that needle tip 114 moves out from catheter distal end 125 to pierce a target tissue site in proximity to distal end 125. In one aspect, the plunger 105 and fitting 104 can include radially extending surfaces 5 and 4, respectively. The surfaces 4 and 5 can facilitate handling of the plunger for performing this operation.

It is noted that although a modular delivery catheter 120 with a non-deflectable configuration is illustrated in FIG. 2, any delivery catheter can be coupled to the actuator 100 via a connector 17, such as a luer coupling. The delivery catheter 120 can be replaced by a catheter selected from a group of deflectable/steerable catheters known to those skilled in the art, for example steerable catheters that include manipulator means incorporated into a handle, i.e. handle 122 illustrated in FIG. 2, the manipulator means causing deflection of catheter shaft 123 to facilitate positioning of the catheter distal end 125 at the target tissue site. An exemplary steerable and deflectable catheter 128 incorporating a navigation insert 52 for use with the navigation system 10 is illustrated in FIG. 3A, and is available from Medtronic, Inc., Minneapolis, Minn. The deflectable/steerable catheter 128 can include a handle 121 with a steering mechanism for bending the shaft of the catheter 128 in various orientations. The navigation insert 52 can include a connector 59 at the distal end of connection cable 57 for connection with the navigation probe interface 50. The navigation insert 52 can also include a fitting 55, such as a luer lock fitting, for connection with the plunger 105 of FIG.

Figure 3:
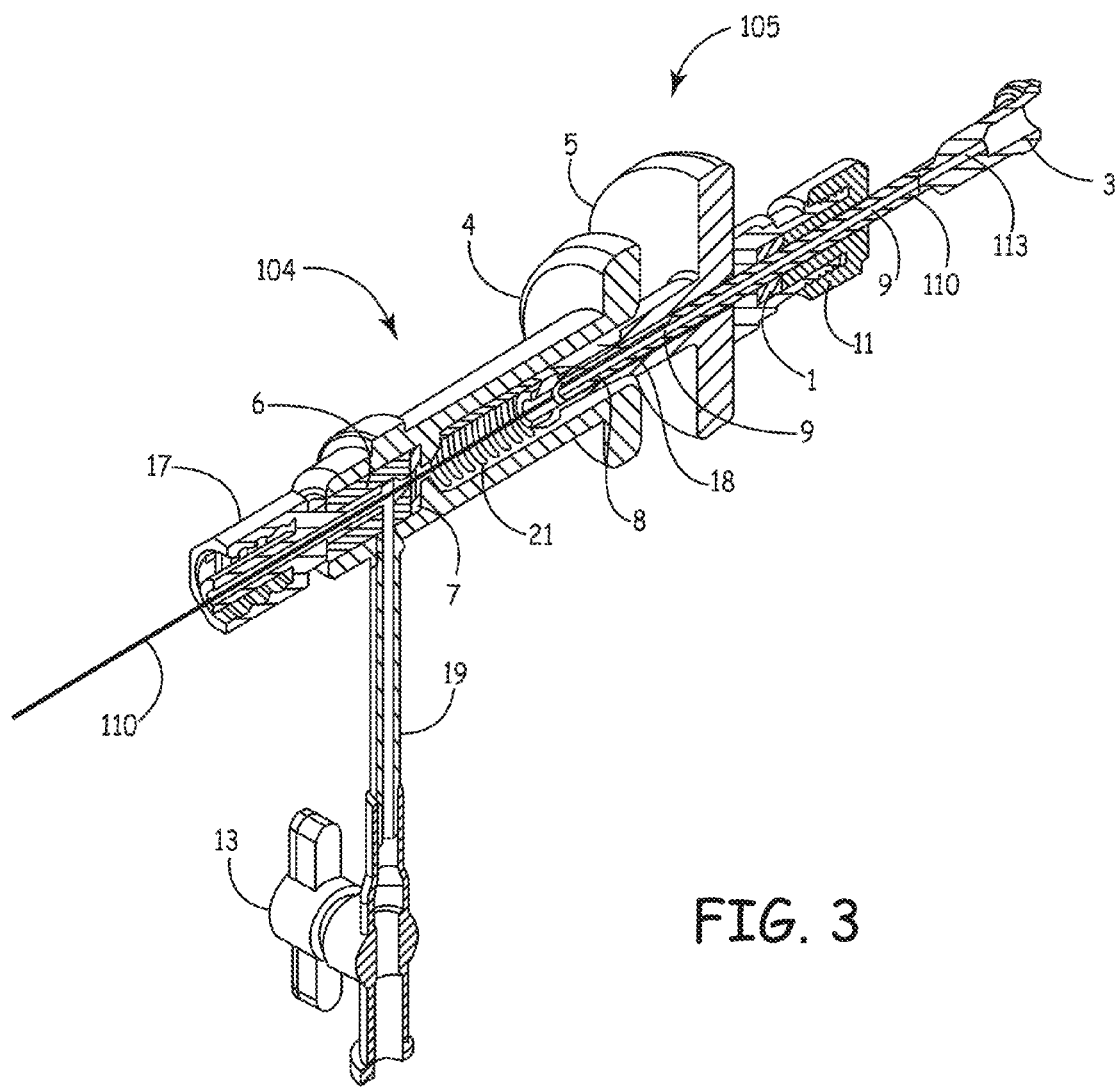
FIG. 3 is a perspective sectional view of an actuator apparatus and injection apparatus of the injection system of FIG. 2.
Figure 3A:
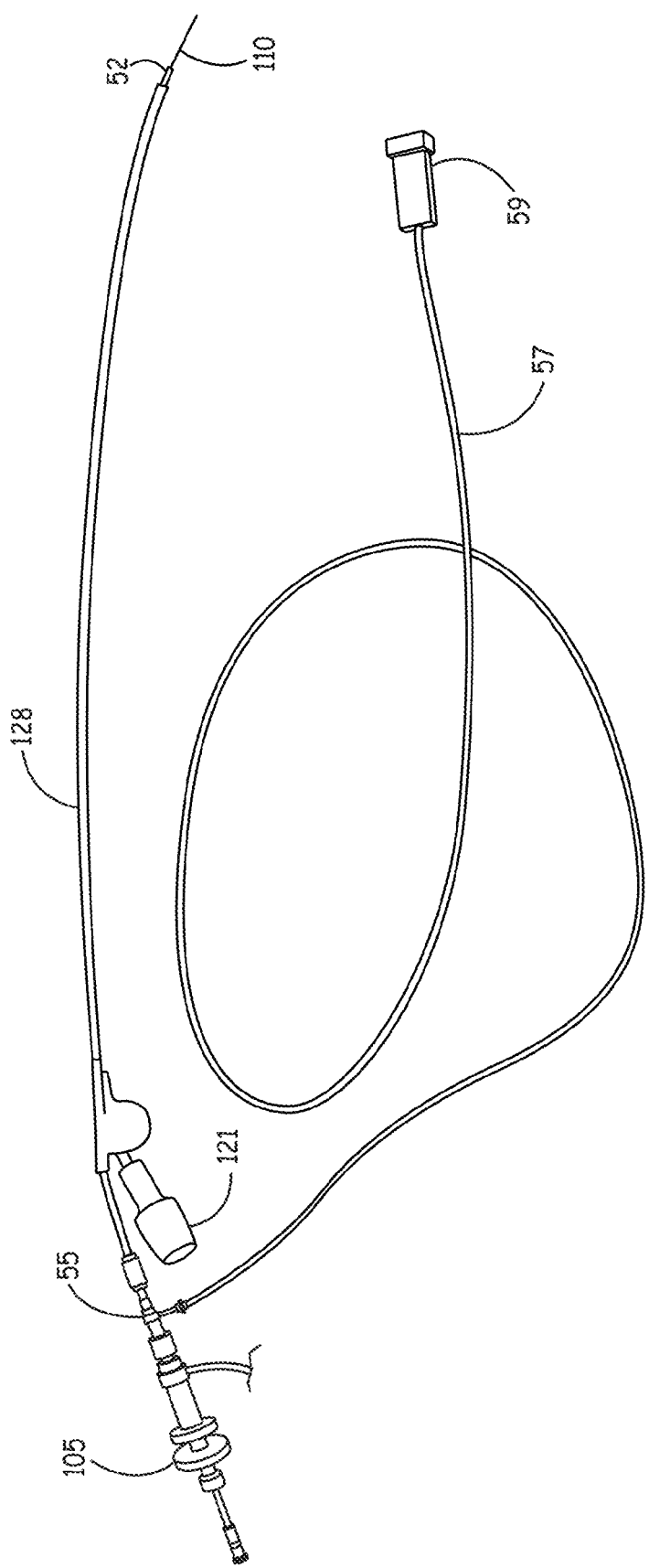
FIG. 3A is a perspective view of an exemplary deflectable/steerable catheter with a navigation insert and the injection apparatus of FIG. 3.
Figure 3B:
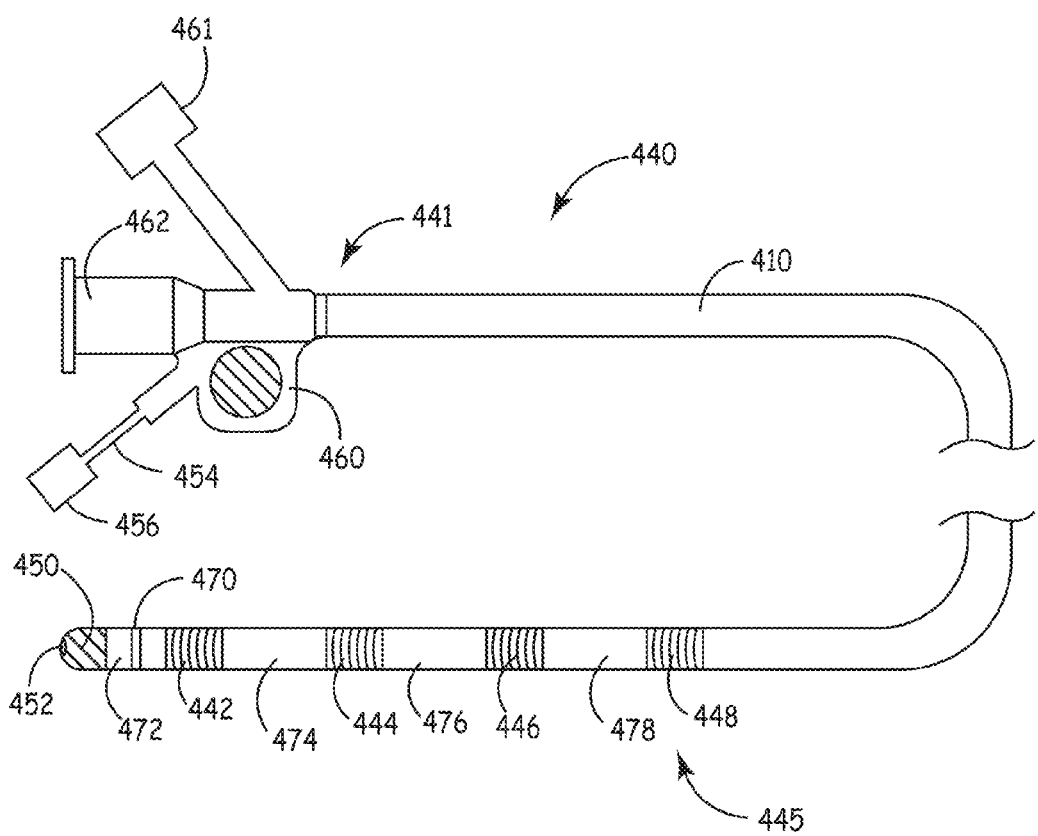
FIG. 3B is a plan view of an integrated navigation/therapy catheter.
Figure 3C:
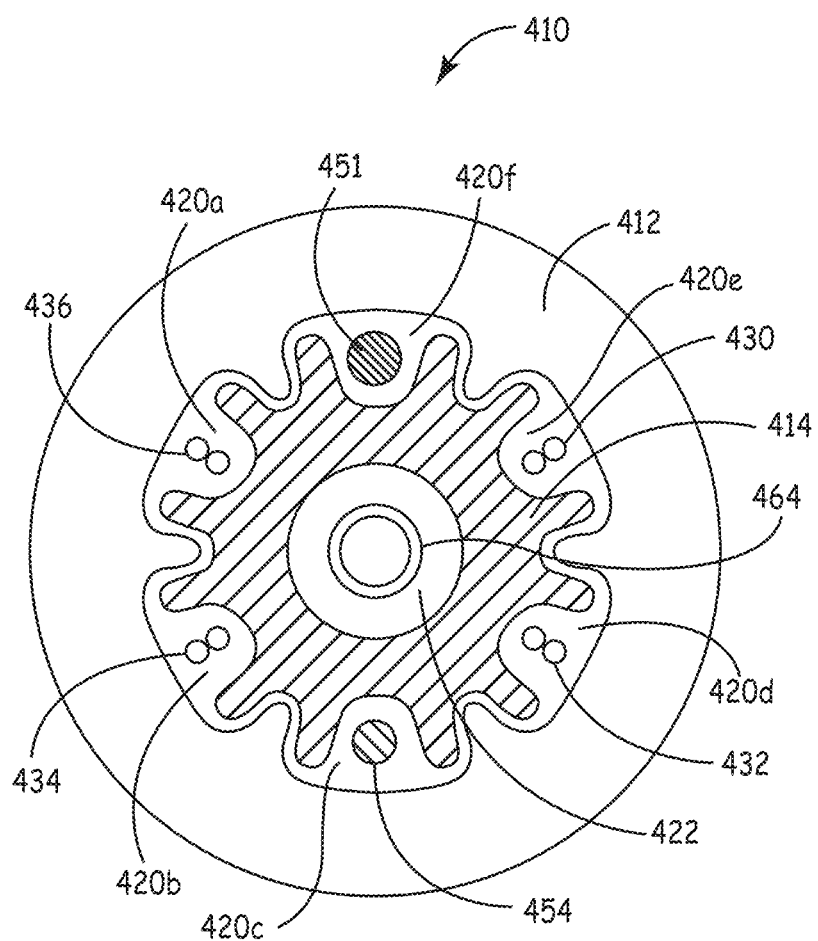
FIG. 3C is a sectional view of the multi-lumen body of the integrated navigation/therapy catheter of FIG. 3B.

FIG. 3 is a perspective sectional view of one exemplary embodiment of actuator apparatus 100 and injection apparatus 110 of the system shown in FIG. 2. FIG. 3 illustrates the injection apparatus 110 having been positioned within the actuator apparatus 100 by passing needle tip 114 (FIG. 2) into opened valve 11, through respective lumens of plunger 105 and fitting 104, and then out through connector 17. According to an exemplary embodiment, molded rigid plastics, examples of which include polycarbonate, polyethylene and polypropylene, can be used to form the plunger 105 and the fitting 104.

With continued reference to FIG. 3, the fitting 104 can include a spring member 21, which is mounted at an interface between the plunger 105 and the fitting 104, and a side port 19, which is terminated by a stopper 13 and is in fluid communication with the lumen of fitting 104, for flushing a lumen of a catheter to which fitting will be coupled. The fitting 104 can include a septum 7, which is held in place by a septum cap 6, for sealing the plunger 105 from the catheter lumen, while allowing passage of injection apparatus 110 therethrough. According to the illustrated embodiment, the spring member 21 holds the plunger 105 in a retracted position until a force is applied to slide plunger 105 distally with respect to the fitting 104. When this force is applied, the valve 11, which is illustrated here as a Touhy-Borst type, will have been tightened, according to means known to those skilled in the art, such that internal walls of a compressible member 1 protrude into the lumen of plunger 105 to grip the injection apparatus 110 so that injection apparatus 110 is advanced distally along with plunger 105. It should be noted that the scope of the present teachings covers other means for reversibly gripping injection apparatus 110 known to those skilled in the art, examples of which include, but are not limited to, 3-jaw chucks and set screws. FIG. 3 further illustrates the injection apparatus 110 including a grip tube 9 positioned around a shaft 112 and enlarging an outer diameter of the shaft 112 to facilitate gripping of the injection apparatus 110 by the valve 11. The grip tube 9 may further enhance gripping by means of a corrugated or soft and/or tacky outer surface.

Referring to FIG. 2, the injection apparatus 110 can be advanced through catheter shaft 123 as follows. Upon coupling actuator 100 to catheter 120, an operator may advance the injection apparatus 110 through the catheter 120 until the needle tip 114 is approximately flush with the catheter distal end 125, at which time valve 11 is closed to grip the injection apparatus 110. Thus, the injection apparatus 110 is held in place within the catheter 120 while the operator advances the catheter 120 to a target tissue site. Once the operator has positioned the catheter distal end 125 in close proximity to the target site, the operator causes the plunger 105 to advance distally, thereby pushing needle tip 114 of injection apparatus 110 into the site. Either in conjunction with or following plunger action, a therapeutic agent with or without a contrast agent can be injected through the injection apparatus 110 from a source of therapeutic agent/contrast mix which is coupled to the injection apparatus 110, via fitting 3. According to the embodiment illustrated in FIG. 3, the actuator apparatus 100 can includes a stop in the form of a pin 8 extending into the fitting 104 and interfacing with a depression 18 formed on the plunger 105. The stop or pin 8 is designed to limit the plunger travel according to a prescribed injection depth. Finally, after injection of the therapeutic agent/contrast mix is completed, the operator allows the plunger 105 to retract by means of the spring force of the spring member 21, as previously described.

Referring to FIG. 3A, the plunger 105 and injection apparatus 110 of FIG. 3 can be used with the deflectable/steerable catheter 128 of FIG. 3A. Alternatively, the integrated steerable navigation/therapy delivery catheter 440 illustrated in FIGS. 3B and 3C can be used in connection with the navigation system 10 for delivering therapeutic agents at the target site according to the present teachings.

FIG. 3B is a plan view of an integrated navigable guide catheter provided with a multilumen lead body including splined inner and outer insulating members. As illustrated in FIG. 3B, integrated catheter 440 is a navigable, steerable catheter having a manipulative handle 460, a shielded connector assembly 461, and an access hub 462 at a proximal end 441 of integrated catheter 440. Multiple location sensors 442, 444, 446 and 448 can be affixed along a distal end 445 of integrated catheter 440 and spaced axially from one another. Location sensors 442, 444, 446, and 448 can be provided as electrically conductive coils formed from fine copper wire in which current is induced by an electromagnetic source located externally to the patient. If braiding is included in outer insulating member 412, it can be terminated proximal to sensor 448 to avoid shielding sensors 442, 444, 446 and 448. The use of electromagnetic coils as location sensors on a navigable catheter is generally disclosed in co-pending U.S. patent application Ser. No. 10/299,969 (2004-0097806), as referenced above. In another aspect, mapping electrodes can be provided for measuring a voltage signal having components corresponding to three orthogonal current signals applied through the patient as generally disclosed in U.S. Pat. No. 5,983,126 issued Nov. 9, 1999, and incorporated herein by reference.

An end cap member 450 can seals the distal end 445 of the multiple lumens of body 410 of integrated catheter 440 against the ingress of body fluids. The end cap member 450 can be formed from a biocompatible polymer material and may be over-molded onto the distal end of body 410. The end cap member 450 can include an opening 452 to a generally central lumen extending within catheter body 410 such that a medical device or therapy delivered through the central lumen may exit through opening 452. The end cap member 450 may alternatively be formed from a conductive biocompatible metal, such as stainless steel, platinum, iridium, titanium, or alloys thereof, and serve as an electrode for sensing cardiac signals, or other electrophysiological signals. The integrated catheter 440 may alternatively or additionally be equipped with additional electrodes or one or more sensors of other types of physiological signals. Other types of physiologic sensors that may be included on catheter body 410 include absolute pressure sensors, temperature sensors (thermocouple or infrared), oxygen sensors, pH sensors, acoustical sensors, etc.

FIG. 3C is a sectional view of an arrangement of multiple conductors within multilumen body 410 included in the integrated catheter 440. An inner insulating member 414 can include a generally central, open lumen 422 through which a medical device 464 or medical therapy may be delivered. The open lumen 422 is accessible via access hub 462 (shown in FIG. 3B) at the proximal end 441 of body 410. As illustrated in FIG. 3C, the medical device 464 can be a hollow needle for use in delivering of a pharmaceutical, genetic, or biologic agent in a liquid medium, although other medical devices, such as cardiac pacing or defibrillation leads, ablation catheters, sensors, etc. may alternatively or additionally be delivered through lumen 422. Thus the integrated catheter 440 may serve multiple purposes during a diagnostic and/or therapy delivery procedure A conductor 451 that extends through lumen 420f can be electrically coupled to end cap member 450, which can also serve as an electrode. Each of four pairs of twisted conductors 430, 432, 434 and 436 extend through a respective lumen 420a, 420b, 420d, and 420e to one of location sensors 442, 444, 446, and 448. The proximal ends of the conductors 430, 432, 434, 436 and 450 are coupled to the shielded connector assembly 461. The connector assembly 461 is provided for connection of the integrated catheter 440 to an external monitor or sensor interface for monitoring signals received from location sensors 442, 444, 446, and 448 and electrode 450. A pull wire 454 extends through lumen 420c. The pull wire 454 can be a high-tensile grade stainless steel wire that is fixedly attached at or near the distal end 445 of the integrated catheter 440. An anchoring member 470 can be a generally ring shaped member encircling the outer circumference of body 410 near the distal end 445 of the integrated catheter 440. The pull wire 454 may be fixedly attached, by welding or other appropriate bonding or joining methods, to anchoring member 470. Anchoring member 470 may optionally serve as an electrode with the pull wire 454 serving additionally as a conductive element to carry electrical current between anchoring member 470 and a proximal connector assembly 461.

The pull wire 454 can extends from the proximal manipulative handle 460 in FIG. 3B to the anchoring member 470 and can be provided with a grip 456 for applying tension to the pull wire 454 to cause deflection of the distal end 445 of the integrated catheter 440. The distal end 445 of the catheter body 410 shown in FIG. 3B can be provided with relatively greater flexibility than the remainder of the catheter body 410. The outer insulating member 412 includes outer insulating segments 472, 474, 476, and 478 positioned along the distal end 445 of the multilumen body 410, which are preferably formed from a lower durometer polymer than the remainder of the catheter body 410.

Having described an exemplary navigation system 10, an exemplary modular (non-deflectable) injection delivery catheter 120, a deflectable steerable injection delivery catheter 128 and injection apparatus 110 in reference with FIGS. 1-3A, and an exemplary integrated steerable navigation/delivery catheter 440 in connection with FIGS. 3B and 3C, a method for therapy delivery by injection is described in reference with FIGS. 4-13. Specifically, a therapeutic agent including a pharmacological, biologic, genetic agent in a liquid medium can be injected into a target site, such as a myocardial infarct site. The therapeutic agent can include, for example, autologous skeletal myoblast cells; autologous bone-marrow cells; stem cells; progenitor cells; cells, molecules or viruses carrying DNA or RNA material; or other agents for molecular or cellular cardiac therapy. Other examples of cell types can generally include islet cells, pluripotent stem cells, mesenchymal stem cells, endodermal stem cells, ectodermal stem cells, hepatocytes, chondrocytes, osteoblasts, neuronal cells, glial cells, smooth muscle cells, endothelial cells, skeletal myoblasts, myoblasts, macrophages, erythrocytes, platelets, and fibroblasts.

Catheter-based injection therapy using cells for cardiac regeneration or cardiac therapy is currently undergoing active preclinical or clinical investigation. Recent investigations include the use therapeutic cell injection of the use of autologous skeletal myoblasts as a standalone procedure in post myocardial infarction chronic heart patients, or as a primary treatment of ischemic heart failure. See for example, Beeri et al, New Efficient Catheter-Based System for Myocardial Gene Delivery, *Circulation,* 2002, 106:1756-1759; Opie and Dib, Surgical and Catheter Delivery of Autologous Myoblasts in Patients with Congestive Heart Failure, *Nature Clinical Practice, Cardiovascular Medicine*, Mar. 3, 2006, (Supp. 1):S42-S45; Perin and Silva, Stem Cell Therapy in End-Stage Ischaemic Heart Failure: A Catheter-Based Therapeutic Strategy Targeting Myocardial Viability, *European Heart Journal Supplements* 2006, 8 (Supp. H):H46-H51; Sherman et al, Catheter-Based Delivery of Cells to the Heart, *Nature Clinical Practice, Cardiovascular Medicine*, Mar. 3, 2006, Supp. 1):S57-S84; Sherman, Warren, Cell Therapy in the Cath Lab for Heart Failure: A Look at MyoCell® Therapy and the SEISMIC Trial, Cath Lab Digest, May 16, 2008, (5):1-4; Smits et al, Catheter-Based Intramyocardial Injection of Autologous Skeletal Myoblasts as a Primary Treatment of Ischemic Heart Failure: Clinical Experience with Six-Month Follow-Up, *J. Am. Coll. Cardiol.,* 2003, 42:2063-2069; and Smits et al, Myocardial Repair by Percutaneous Cell Transplantation of Autologous Skeletal Myoblast as a Stand Alone Procedure in Post Myocardial Infarction Chronic Heart Failure Patients, *EuroInterv.* 2006, 1:417-424.

The present teachings provide a method for ascertaining that the therapeutic agents are delivered to and implanted in the target site and cover the entire target area. According to the present teachings, the therapeutic agents are mixed with a contrast agent. The contrast agent can be selected with regard to the particular imaging system used during the procedure. For fluoroscopic imaging, the contrast agent can be, for example, Isovue® (iopamidole injection) commercially available from Bracco Diagnostics, Inc., Princeton, N.J., or any other suitable X-ray contrast agent. For MR imaging, the contrast agent can be replaced by a gadolinium enhanced carrier fluid. The amount of contrast agent included in the mix is selected to provide adequate visibility of the injection locations. A mix of 10-20% contrast agent to therapeutic agent can be generally sufficient, although the exact percentages depend on the contrast agent and injection volume.

When the therapeutic agent/contrast mix is injected to the target site using the navigation and delivery systems described above or equivalent systems, a dispersion cloud is visible in fluoroscopic images obtained after injection. The image of the dispersion cloud generally represents the dispersion area of the contrast agent. The dispersion area of the contrast agent is not necessarily equal to and does not necessarily coincide with the dispersion area of the therapeutic agent. The present teachings provide a method for determining the dispersion area of the therapeutic agent from the image of the dispersion area of the contrast agent, and interactively covering or populating the target site with the therapeutic agent.

Figure 4:
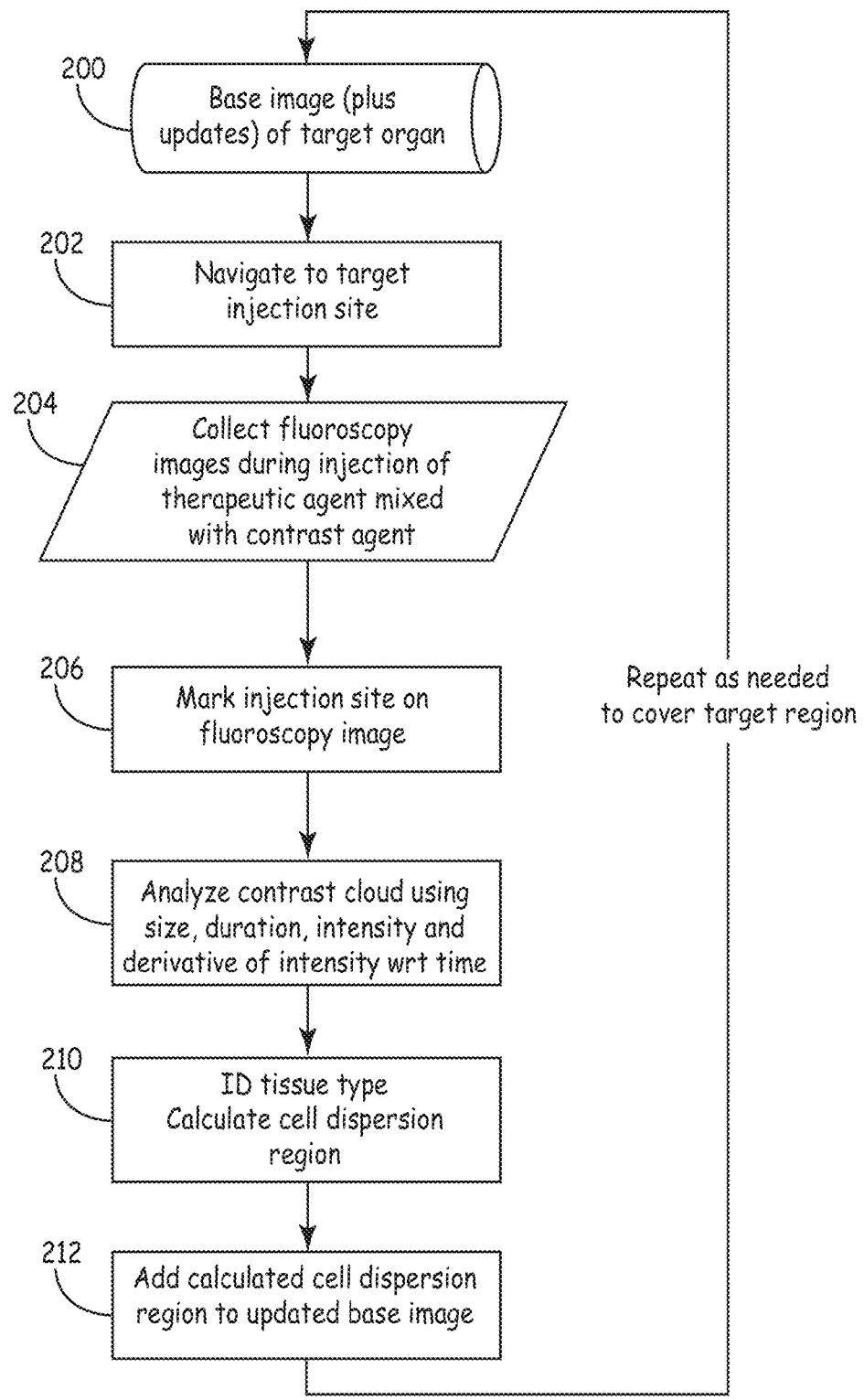
FIG. 4 is a flowchart of a method of interactively determining a therapy dispersion region according to the present teachings.
Figure 4A:
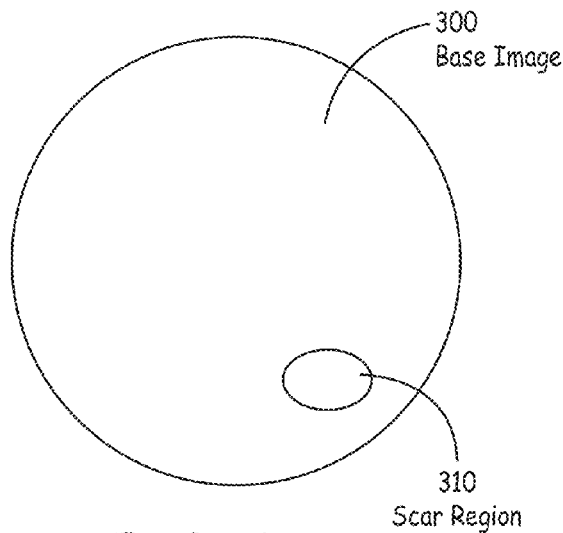
FIG. 4A is a base image of a target organ with an image of the damaged issue overlaid thereon according to the present teachings.
Figure 4B:
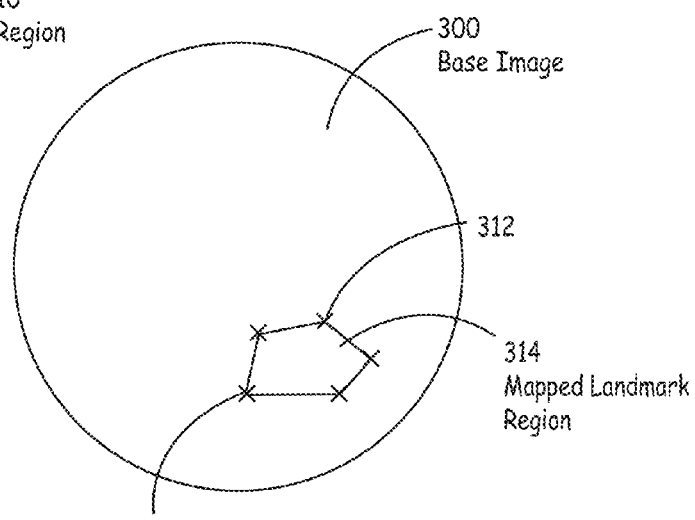
FIG. 4B is a base image of a target organ showing a target region marked with mapped landmarks according to the present teachings.

Referring to FIGS. 4, and FIGS. 4A to 4C, a base image 300 of the target organ can be first obtained at 200. The base image 300 can be, for example, a pre-acquired fluoroscopic image of the target organ of the patient, such as, for example, the heart. The target area 310 can be a myocardial infarction scar or other damaged tissue or tissue targeted for treatment by injection of therapeutic agents. The target area 310 can be identified by various techniques, and marked on the base image 300. For example, the target area can be mapped electrically by obtaining electrograms (EGM) of a normal organ/tissue and comparing with electrograms of diseased organ/tissue. Specifically, an electrophysiological mapping catheter, such as the integrated catheter 440 equipped with mapping electrodes, as discussed above, can be inserted into the cardiac tissue, and the signals produced thereby may then be reviewed using known EGM mapping methods to determine abnormalities indicating diseased tissue. Alternatively, a target volume can be identified in functional 3D images of infarcted myocardium by perfusion imaging with MR, PET or with PET/CT. The target area 310 can be identified on the respective fluoroscopic base image 300 to navigate to and inject the cell-based therapy. Referring to FIG. 4A, the target area 310, such as a scar region, can be projected onto the base image 300 from a functional 3D image data set using image merging, as discussed above in connection with the navigation system 10. Alternatively, and referring to FIG. 4B, landmarks 312 from a mapping procedure performed immediately prior to the cell injections can be established on the base image 300 and connected with lines to enclose an area 314 to be treated as the target area 310.

Referring to FIG. 4, after the target area 310 is identified on the fluoroscopic base image 300, the electromagnetic/navigation catheter 52 inside the delivery catheter 120 is guided to the target area 310, at 202. A first therapeutic dose of the therapeutic agent/contrast mix is injected into the target area 310, and fluoroscopic images of the target area are taken and collected during and after the injection at specific intervals, at 204. Representative images taken at time T=0, or immediately upon injection, and after time T=5 min has elapsed, for various types of tissue are illustrated in FIGS. 5C, 5D, 9C and 9D, in which the contrast agent dispersion cloud is represented at 350. FIGS. 7C and 8C illustrate, respectively, images taken at time T=0 for blood in cardiac chamber and blood in heart vessel. For these tissue types, the contrast agent dispersion cloud 350 substantially disappears by time T=5 min and the images are the same as the base images without any dispersion cloud visible.

Figure 5A:
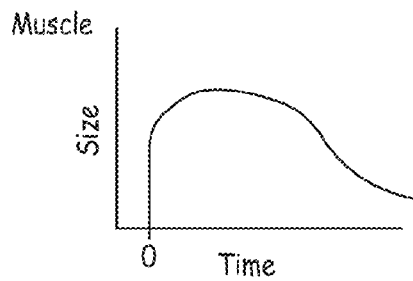
FIG. 5A is a representative size vs. time graph for a contrast dispersion cloud in muscle tissue according to the present teachings.
Figure 5B:
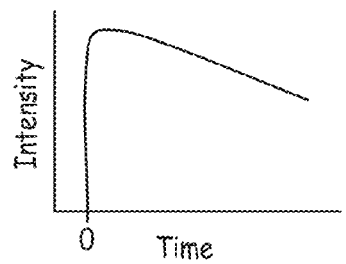
FIG. 5B is a representative intensity vs. time graph for a contrast dispersion cloud in muscle tissue according to the present teachings.
Figure 6A:
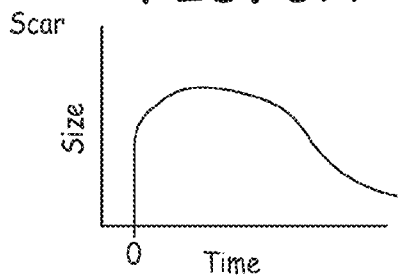
FIG. 6A is a representative size vs. time graph for a contrast dispersion cloud in scar tissue according to the present teachings.
Figure 6B:
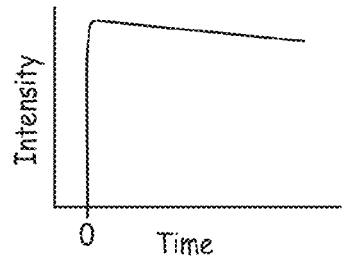
FIG. 6B is a representative intensity vs. time graph for a contrast dispersion cloud in scar tissue according to the present teachings.
Figure 7A:
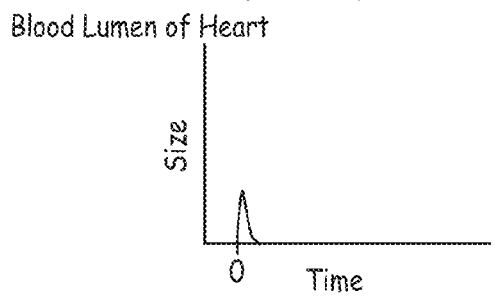
FIG. 7A is a representative size vs. time graph for a contrast dispersion cloud in a blood-filled cardiac chamber according to the present teachings.
Figure 7B:
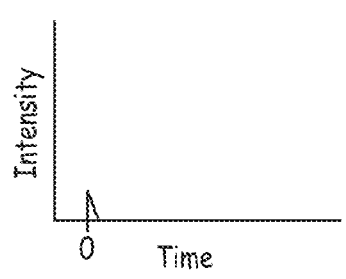
FIG. 7B is a representative intensity vs. time graph for a contrast dispersion cloud in a blood-filled cardiac chamber according to the present teachings.
Figure 8A:
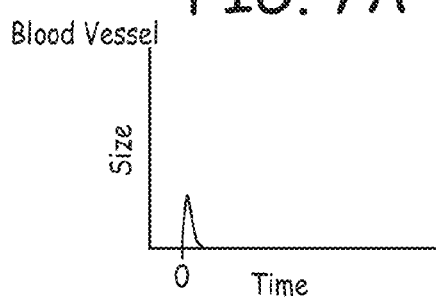
FIG. 8A is a representative size vs. time graph for a contrast dispersion cloud in a cardiac blood vessel according to the present teachings.
Figure 8B:
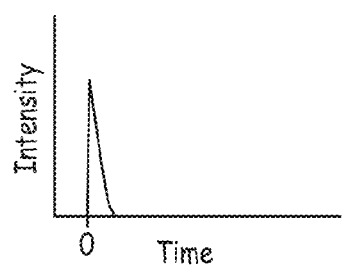
FIG. 8B is a representative intensity vs. time graph for a contrast dispersion cloud in a cardiac blood vessel according to the present teachings.
Figure 9A:
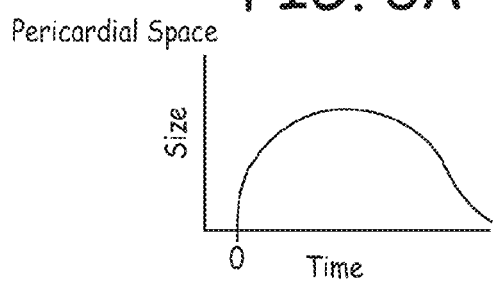
FIG. 9A is a representative size vs. time graph for a contrast dispersion cloud in pericardial space according to the present teachings.
Figure 9B:
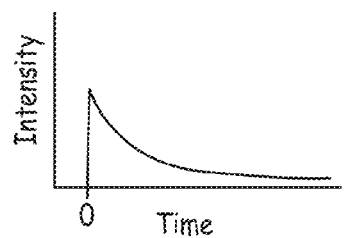
FIG. 9B is a representative intensity vs. time graph for a contrast dispersion cloud in pericardial space according to the present teachings.
Figure 5C:
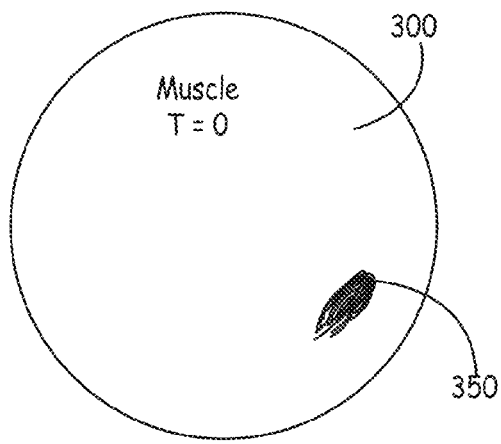
FIG. 5C is a diagrammatic representation of a contrast dispersion cloud in muscle tissue at time T=0 according to the present teachings.
Figure 5D:
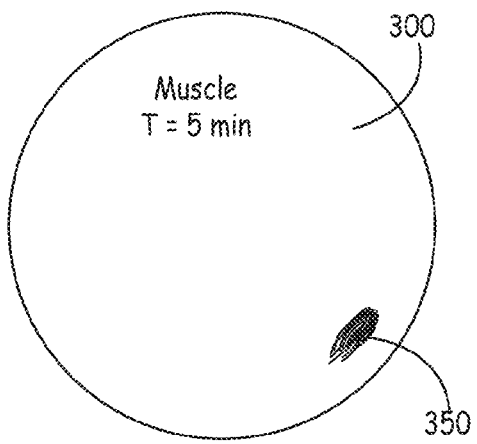
FIG. 5D is a diagrammatic representation of a contrast dispersion cloud in muscle tissue at time T=5 min according to the present teachings.
Figure 9C:
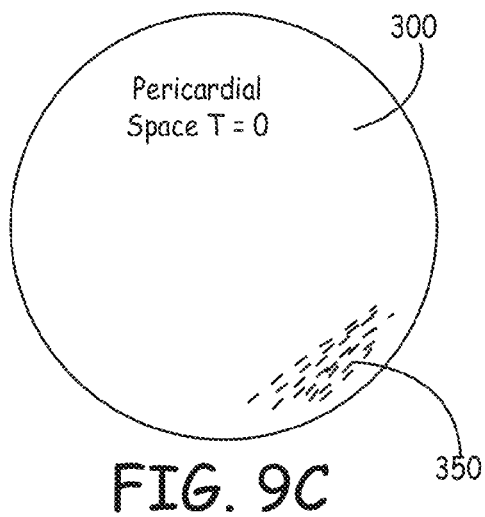
FIG. 9C is a diagrammatic representation of a contrast dispersion cloud in pericardial space at time T=0 according to the present teachings.
Figure 9D:
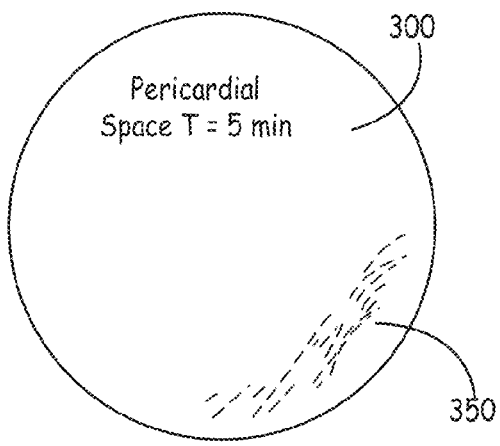
FIG. 9D is a diagrammatic representation of a contrast dispersion cloud in pericardial space at time T=5 min according to the present teachings.
Figure 7C:
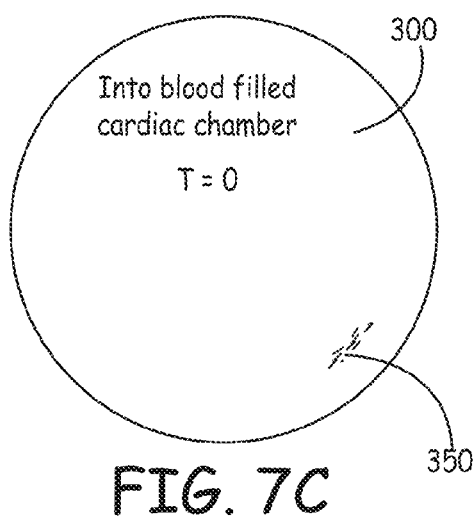
FIG. 7C is a diagrammatic representation of a contrast dispersion cloud in a blood-filled cardiac chamber at time T=0 according to the present teachings.
Figure 8C:
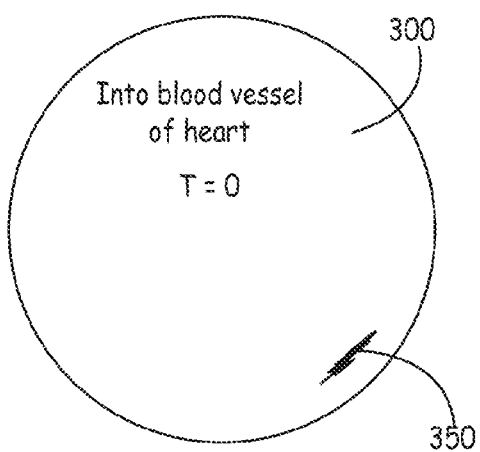
FIG. 8C is a diagrammatic representation of a contrast dispersion cloud in a cardiac blood vessel at time T=0 according to the present teachings.

By taking and comparing a plurality of fluoroscopic images, the size and intensity of the contrast cloud can be plotted over time for various tissue types, such as in muscle tissue, illustrated in FIGS. 5A and 5B; in scar or infarct tissue, illustrated in FIGS. 6A and 6B; in blood lumen of heart (blood-filled cardiac chamber), illustrated in FIGS. 7A and 7B; in blood vessel, illustrated in FIGS. 8A and 8B; and in pericardial space, illustrated in FIGS. 9A and 9B. As can be seen from these figures, the size of the contrast agent dispersion cloud 350, gradually reaches a peak value and gradually decreases for muscle, scar and pericardial space, as illustrated in FIGS. 5A, 6A, and 9A. The intensity "I" of the contrast dispersion cloud 350 decreases gradually from a peak value for muscle (FIG. 5B) and scar tissue (FIG. 6B), and rapidly for pericardial space (FIG. 9B). The size and intensity of the contrast dispersion cloud rise and fall rapidly in blood of lumen of heart (FIGS. 7A and 7B) or in blood vessel (FIGS. 8A and 8B), the intensity of the contrast dispersion cloud 350 being higher for injection in blood vessel than in blood of lumen of the heart. These results are also summarized in Table 1 of FIG. 10, which also includes a characterization of the slope (derivative dI/dt) of the intensity vs., time diagrams. It is noted that the graphs of size vs. time are determined at a given level intensity of the contrast dispersion cloud greater than a threshold value.

Figure 4C:
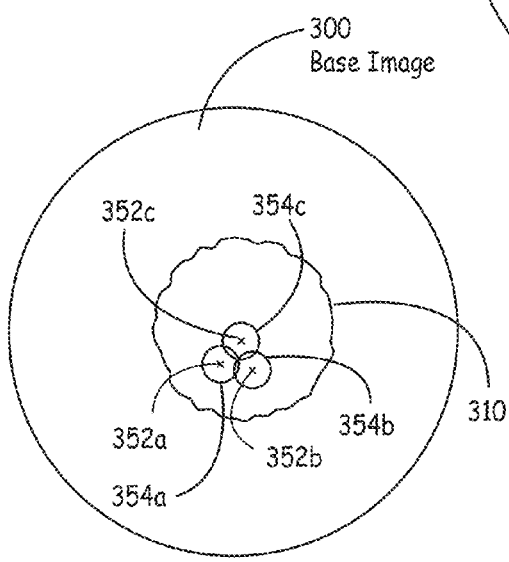
FIG. 4C is a base image of a target organ showing consecutive injection locations and calculated cell dispersion areas according to the present teachings.

Referring to FIG. 4, at 206, the first injection location is marked in the fluoroscopic image 300 at 352a, as shown in FIG. 4C. The characteristics of the contrast dispersion cloud 350 can then be analyzed at 208, using the radiographic images, the size vs. time and intensity vs. time graphs, Table 1 of FIG. 10 to determine the type of tissue reached at the first injection location. The area $A_{contrast}$ of the contrast dispersion cloud 350 can be calculated at a specific time after injection, for example at time T=5 min. The area $A_{contrast}$ of the contrast dispersion cloud 350 can be correlated with the area $A_{cell}$ of the therapy dispersion via a parameter β, which is estimated experimentally, as follows:

$$A_{cell} = \beta A_{contrast}$$

A range of values for the parameter β based on T=5 min and intensity greater than the threshold value are given in Table 2, illustrated in FIG. 11, for different tissue types. Using the identified tissue type and the corresponding value of the parameter β, the area of the therapeutic agent dispersion can be determined (at 210, FIG. 4) and the therapeutic agent dispersion region 354a can be marked (212, FIG. 4) in FIG. 4C relative to the first injection location 352a. The procedure is then repeated for a second injection location marked at 352b and corresponding therapeutic agent dispersion 354b, a third injection location marked at 352c and corresponding therapeutic agent dispersion 354c, and so on, until the entire target are 310 is covered by overlapping therapeutic agent dispersion regions 354a, 354b, 354c, etc.

Referring to Table 2 of FIG. 11, for tissue in the pericardial space in the blood filled lumen of the heart, the parameter β is substantially zero and, therefore, no dispersion area for the therapeutic agent is marked relative to the first injection location 352a in FIG. 4C. The injection is repeated at a second location 352b adjacent to the first injection location 352a, and so on.

Figure 12:
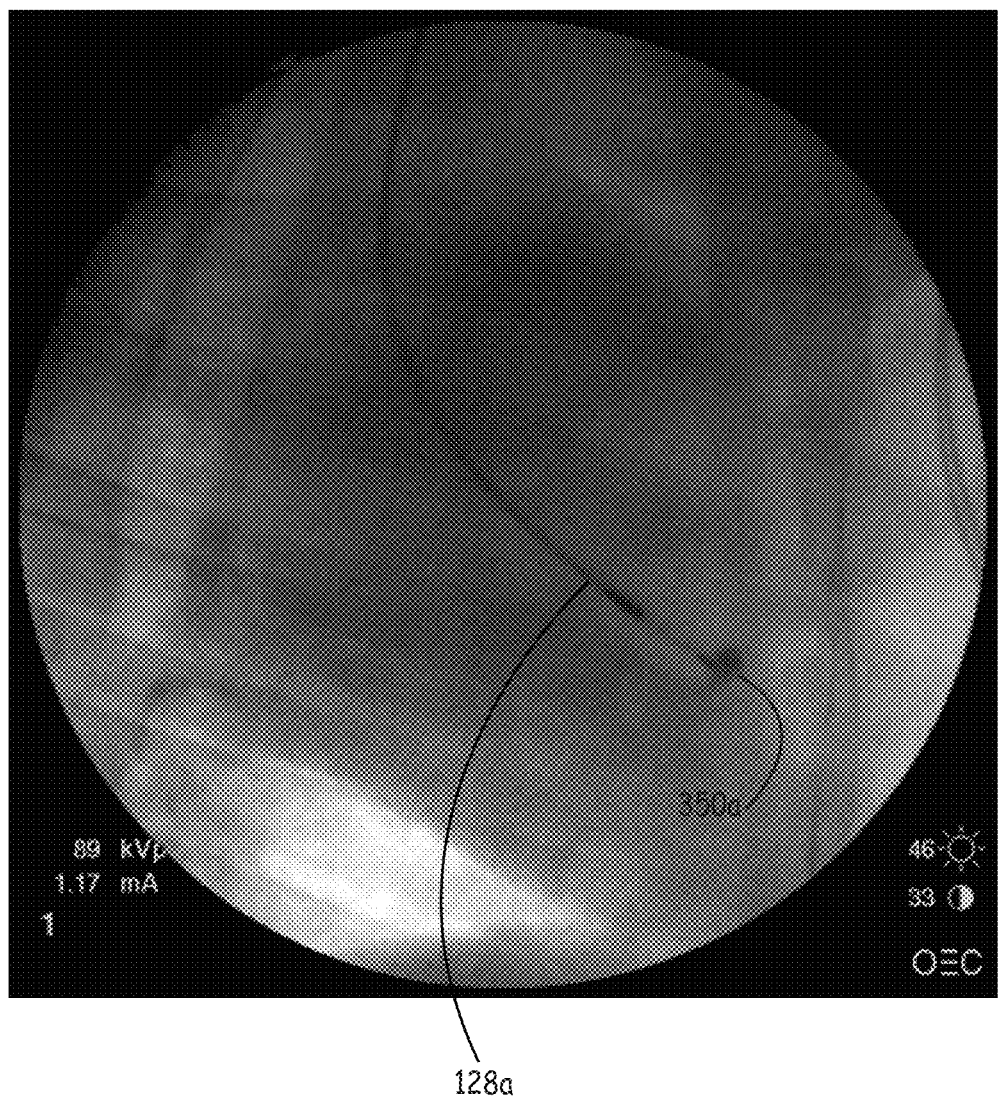
FIG. 12 is a radiographic image showing a contrast dispersion cloud at time T1 according to the present teachings.
Figure 13:
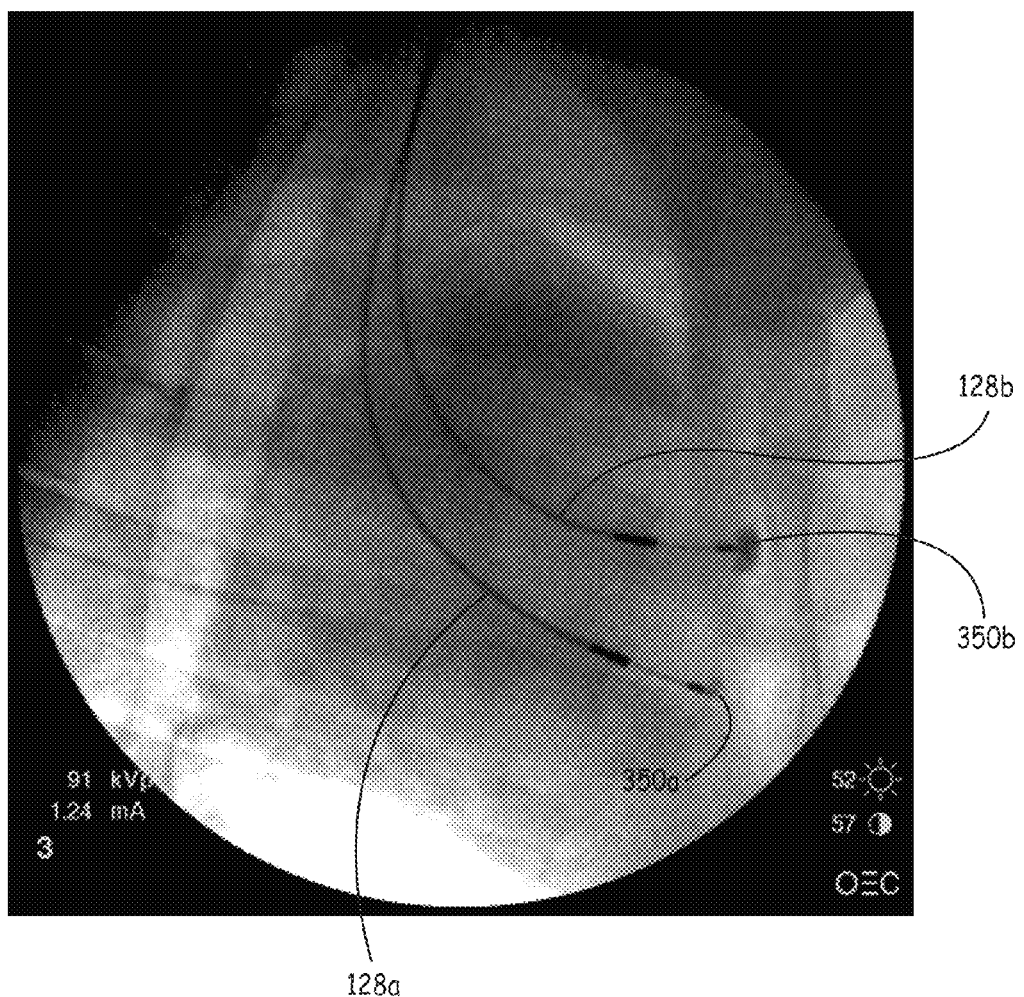
FIG. 13 is a radiographic image showing the contrast dispersion cloud of FIG. 12 at time T2 and a second contrast dispersion cloud injected at time T2 according to the present teachings.

It will be appreciated that although the above procedure has been described in terms of determining areas of dispersion based on a using a two-dimensional image collection systems, the present teachings can also be used with a three-dimensional image collection system, in which volumes of contrast dispersion can be determined from the images and a therapeutic agent dispersion volume can be obtained by corresponding experimental volumetric parameter β. For example, single plane fluoroscopy can provide visible cloud area, while biplane fluoroscopy can provide two two-dimensional images, which, when perpendicular to one another, can provide an estimate of cloud volume. It is also noted that although an isocentric C-arm used in rotational angiography can provide a cloud map, the image acquisition process can take about 20 seconds, while dispersion is occurring during the image acquisition. Additionally, gadolinium enhanced MR imaging can provide a visible cloud volume. Exemplary two-dimensional radiographic images are illustrated in FIGS. 12 and 13. FIG. 12 is a radiographic image showing a contrast dispersion cloud 350a immediately after injection at time T=0. FIG. 13 is a radiographic image showing the contrast dispersion cloud 350a of FIG. 12 at time T=5 min and a second contrast dispersion cloud 350b injected at time T=5 min. In the particular procedure illustrated in FIGS. 12 and 13, two implantable catheters 128a, 128b are used.

When the imaging modality is Magnetic Resonance Imaging (MRI), such as, for example, a gadolinium enhanced MRI, an MRI carrier fluid for the therapeutic agent takes the place the contrast agent, and the time series of images show a progression of an edema region rather than a contrast agent dispersion cloud. The procedure for populating the target site is followed as discussed above. The inclusive term "imaging agent" can stand for the contrast agent of fluoroscopic imaging or for the MRI carrier fluid. Similarly, the inclusive term "imaging agent visible region" can stand for the contrast agent dispersion cloud or the MRI edema region.

As discussed above, the present teachings provide a method of populating a target site in an organ with therapeutic agents. The method can be used interactively to monitor the progression of the therapeutic dispersion region and continue injection in adjacent locations within the target site. The method can be used in an injection mix of an imaging agent with any selected therapeutic agent. The method can also be used with any navigation system and navigation/injection/delivery catheter, as described above in exemplary illustrations of the method.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A method of delivering therapy to a target site, the method comprising:
   (a) obtaining a base image of the target site;
   (b) navigating a catheter to the target site;
   (c) injecting a dose of a mix of a therapeutic agent and a contrast agent into a first injection location at the target site;
   (d) collecting sequential fluoroscopic images of a contrast agent dispersion cloud at the first injection location;
   (e) determining a contrast agent dispersion region from the sequential fluoroscopic images;
   (f) identifying a tissue type of the first injection location;
   (g) determining a therapeutic agent dispersion region from the contrast agent dispersion region;
   (h) marking the therapeutic agent dispersion region on the base image of the target site; and (i) repeating (b) through (h) until the target site is substantially covered with overlapping therapeutic agent dispersion regions corresponding to a plurality of injections at a plurality of injection locations at the target site,
wherein a plurality of the therapeutic agent dispersion regions are presented on the base image at the same time.

2. The method of claim 1, wherein determining a contrast agent dispersion region includes determining a size of the contrast agent dispersion cloud as a function of time.

3. The method of claim 2, wherein determining a contrast agent dispersion region includes determining a duration of the contrast agent dispersion cloud as a function of time.

4. The method of claim 3, wherein determining a contrast agent dispersion region includes determining an intensity of the contrast agent dispersion cloud as a function of time.

5. The method of claim 4, wherein determining a contrast agent dispersion region includes determining a time derivative of intensity of the contrast agent dispersion cloud as a function of time.

6. The method of claim 1, wherein determining a therapeutic agent dispersion region from the contrast agent dispersion region comprises determining a therapeutic agent dispersion area from the contrast agent dispersion area using two-dimensional fluoroscopic images.

7. The method of claim 6, wherein determining a therapeutic agent dispersion area from the contrast agent dispersion area comprises correlating the therapeutic agent dispersion area and the contrast agent dispersion with a parameter that depends on a tissue type of the injection location.

8. The method of claim 1, wherein injecting a dose of a mix of a therapeutic agent and a contrast agent into a first injection location at the target site comprises injecting a dose through an injection needle, the injection needle passing through a deflectable catheter, the deflectable catheter including a removable navigation insert.

9. The method of claim 1, wherein injecting a dose of a mix of a therapeutic agent and a contrast agent into a first injection location at the target site comprises injecting a dose through an injection needle, the injection needle passing through an integrated deflectable multi-lumen navigation/therapy delivery catheter.

10. The method of claim 1, wherein the therapeutic agent comprises at least one of the following types of cells: islet cells, pluripotent stem cells, mesenchymal stem cells, endodermal stem cells, ectodermal stem cells, hepatocytes, chondrocytes, osteoblasts, neuronal cells, glial cells, smooth muscle cells, endothelial cells, skeletal myoblasts, myoblasts, macrophages, erythrocytes, platelets, and fibroblasts.

11. The method of claim 1, wherein determining the therapeutic agent dispersion region comprises determining the therapeutic dispersion region based on the tissue type identified at the first injection location in combination with the contrast agent dispersion region.

12. The method of claim 1, wherein identifying a tissue type of the first injection location comprises analysis of the sequential fluoroscopic images of the contrast agent dispersion cloud at the first injection location.

13. A method of delivering therapy to a target site, the method comprising:
obtaining a base image of the target site;
navigating a catheter including a delivery needle to the target site;
injecting through the needle a first dose of a mix of a therapeutic agent and a contrast agent into a first injection location at the target site;
collecting sequential fluoroscopic images of a contrast agent dispersion cloud at the first injection location;
determining a contrast agent dispersion region from the sequential fluoroscopic images of the first injection location;
identifying a tissue type of the first injection location;
determining a therapeutic agent dispersion region from the contrast agent dispersion region of the first injection location;
marking the therapeutic agent dispersion region of the first injection location on the base image of the target site;
injecting through the needle a second dose of a mix of a therapeutic agent and a contrast agent into a second injection location different from the first injection location at the target site; and
determining a therapeutic agent dispersion region for the second injection location and marking the therapeutic agent dispersion region for the second injection location on the base image of the target site, wherein a plurality of the therapeutic agent dispersion regions are presented on the base image at the same time.

14. The method of claim 13, further comprising collecting sequential fluoroscopic images of a contrast agent dispersion cloud at the second injection location.

15. The method of claim 14, further comprising determining a contrast agent dispersion region from the sequential fluoroscopic images at the second injection location.

16. The method of claim 15, further comprising determining a therapeutic agent dispersion region from the contrast agent dispersion region at the second injection location.

17. The method of claim 16, further comprising marking the therapeutic agent dispersion region of the second injection location on the base image of the target site.

18. The method of claim 13, wherein determining the therapeutic agent dispersion region comprises determining the therapeutic dispersion region based on the tissue type identified at the first injection location in combination with the contrast agent dispersion region of the first injection location.

19. The method of claim 13, wherein identifying a tissue type of the first injection location comprises analysis of the sequential fluoroscopic images of the contrast agent dispersion cloud at the first injection location.

* * * * *